(12) United States Patent
Li et al.

(10) Patent No.: US 8,265,884 B2
(45) Date of Patent: Sep. 11, 2012

(54) METHOD TO MEASURE THE ELASTIC MODULUS AND HARDNESS OF THIN FILM ON SUBSTRATE BY NANOINDENTATION

(75) Inventors: Han Li, Cambridge, MA (US); Joost Vlassak, Lexington, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 519 days.

(21) Appl. No.: 12/506,648

(22) Filed: Jul. 21, 2009

(65) Prior Publication Data

US 2010/0024534 A1    Feb. 4, 2010

Related U.S. Application Data

(60) Provisional application No. 61/084,288, filed on Jul. 29, 2008.

(51) Int. Cl.
- *B82Y 30/00* (2011.01)
- *G01N 33/00* (2006.01)
- *G01N 3/42* (2006.01)

(52) U.S. Cl. ............... 702/33; 73/81; 73/150 R; 73/823; 702/85; 977/956

(58) Field of Classification Search .............. 73/81, 104, 73/150 R, 823; 702/33, 85, 97, 189; 977/956
See application file for complete search history.

(56) References Cited

U.S. PATENT DOCUMENTS

| | | | |
|---|---|---|---|
| 4,848,141 A | 7/1989 | Oliver et al. | |
| 6,053,034 A * | 4/2000 | Tsui et al. | 73/81 |
| 6,339,958 B1 * | 1/2002 | Tsui et al. | 73/150 A |
| 6,883,367 B2 * | 4/2005 | Feng et al. | 73/81 |
| 7,149,634 B2 * | 12/2006 | Ma et al. | 702/41 |
| 2008/0022759 A1 * | 1/2008 | Su et al. | 73/105 |

FOREIGN PATENT DOCUMENTS

| | | | | |
|---|---|---|---|---|
| JP | 01027672 A | * | 1/1989 | 427/8 |
| JP | 2001349815 A | * | 12/2001 | |

OTHER PUBLICATIONS

Yu et al., "The Effect of Substrate on the Elastic Properties of Films Determined by the Indentation Test-Axisymmetric Boussinesq Problem" J. Mech. Phys. Solids, vol. 38, No. 6, pp. 745-764, 1990.
El-Gendi et al., "Chebyshev solution of differential, integral and integro-differential equations" Computer Journal 1969; pp. 282-287.
Oliver et al., "An improved technique for determining hardness and elastic modulus using load and displacement experiments" J. Mater. Res., vol. 7, No. 6, Jun. 1992, 1992 Materials Research Society, pp. 1564-1583.

* cited by examiner

*Primary Examiner* — Thomas P Noland
(74) *Attorney, Agent, or Firm* — Gesmer Updegrove LLP (57) ABSTRACT

A method of measuring the elastic modulus and hardness of a thin film on substrate using nanoindentation technique is provided. The method includes calculating a series of experimental corrected stiffness and contact radius pairs associated with one or more presumed parameters and information obtained from a loading curve associated with the thin film and substrate. Also, the method includes calculating a series of theoretical corrected stiffness and contact radius pairs associated with the same one or more presumed parameters and information obtained from the loading curve associated with the thin film and substrate. Furthermore, the method includes using results obtained from the experimental and theoretical corrected stiffness and contact radius pairs to compute the elastic modulus and hardness of the film material.

7 Claims, 11 Drawing Sheets

METHOD TO MEASURE THE ELASTIC MODULUS AND HARDNESS OF THIN FILM ON SUBSTRATE BY NANOINDENTATION

PRIORITY INFORMATION

This application claims priority from provisional application Ser. No. 61/084,288 filed Jul. 29, 2008, which is incorporated herein by reference in its entirety.

BACKGROUND OF THE INVENTION

The invention is related to the field for measuring the mechanical properties of materials, and more specifically to a technique for measuring the elastic modulus and hardness of the thin film in a film-on-substrate system using depth-sensing indentation techniques, also known as nanoindentation.

Nanoindentation techniques have been widely used for measuring the mechanical properties of solids in various forms at small scale. In a typical indentation test, a diamond tip is driven into the specimen surface under controlled load, and the displacement of the indenter tip is continuously monitored with high resolution sensors. Various mechanical properties (most typically the elastic modulus and hardness) of the indented material can be measured by analyzing the indentation data, without the necessity of imaging the indent. Since 1992, the method proposed by Oliver and Pharr has been established as a standard procedure for analyzing indentations performed on monolithic materials, and is generally referred to as the Oliver-Pharr method [1].

Oliver-Pharr method was intended for monolithic solids. The procedure becomes problematic when applied on a film-on-substrate system, where the substrate can be mechanically different from the film material. Significant error can be induced on the estimation of the contact area between the indenter and the specimen, thus affecting the measurement accuracy of the film properties. This is because the indenter detects not only the response of the film, but also that from the substrate. In general, the error due to the substrate effect increases with increasing indentation depth and with increasing elastic mismatch between film and substrate. To minimize the effect of the substrate on the measurement, the indentation depth is often limited to less than 10% of the film thickness. This empirical rule is not always reliable, especially if the elastic mismatch between film and substrate is large. It is also not useful for ultra-thin films when experimental issues make it difficult to obtain reliable measurement from shallow indentations. Evidently there exists a need for a method that can be used to analyze thin-film indentation data for indentation depths where the substrate effect cannot be ignored.

Oliver-Pharr method is based on Sneddon's elastic solution of indenting an elastic half space with a rigid punch. The contact area is estimated by assuming that the contact periphery behaves as described by the elastic solution. Sneddon's solution dictates that the sink-in depth in an elastic indentation is:

$$h_s = \varepsilon \frac{P}{S} \quad (1)$$

where $\varepsilon$ is a constant depending on the punch geometry (e.g. $\varepsilon=0.72$ for conical tip), P is the indentation load, and S is the contact stiffness between the tip and the specimen. S is measured in an unloading process from the peak load since the recovery of material during unloading is mainly elastic. S can also be continuously measured throughout the entire indentation test by imposing a relatively small oscillatory force at high frequency onto the quasi-static load [1, 2].

The sink-in depth is then used to obtain the contact depth according to $$h_c = h - h_s \quad (2)$$

The contact area is calculated from contact depth using the area function of the indenter tip:

$$A_c = f(h_c) \quad (3)$$

The area function $f(h_c)$ describes the cross-section area of the indenter as a function of the distance to its tip and is known a priori. For a conical tip, the contact radius is as follows:

$$a = \sqrt{\frac{A_c}{\pi}} = h_c \cdot \tan(\theta) \quad (4)$$

The reduced indentation modulus $E_r$ is calculated from the contact stiffness S and contact area $A_c$ as follows:

$$E_r = \frac{\sqrt{\pi}}{2} \frac{S}{\sqrt{A_c}} \quad (5)$$

The reduced modulus is related with the elastic constants of the sample as follows:

$$\frac{1}{E_r} = \frac{1-\upsilon^2}{E} + \frac{1-\upsilon_{tip}^2}{E_{tip}} \quad (6)$$

where E and $\upsilon$ is the Young's modulus and Poisson's ratio of the sample, respectively, and $E_{tip}$ and $\upsilon_{tip}$ is the same quantities for the indenter material (usually diamond).

For a film-on-substrate system, however, EQ 1 and 5 are no longer valid, and $h_s$ in general is not equal to $$\varepsilon \frac{P}{S}.$$

Thus, the invention provides a method for measuring the elastic modulus and hardness in film-on-substrate system.

SUMMARY OF THE INVENTION

According to one aspect of the invention, there is provided a method of measuring the elastic modulus and hardness of a thin film on substrate. The method includes calculating a series of experimental corrected stiffness and contact radius pairs associated with one or more presumed parameters and information obtained from a loading curve associated with the thin film and substrate. Also, the method includes calculating a series of theoretical corrected stiffness and contact radius pairs associated with the same one or more presumed parameters and information obtained from the loading curve associated with the thin film and substrate. Furthermore, the method includes using results obtained from the experimental corrected stiffness and contact radius pairs and the theoretical corrected stiffness and contact radius pairs to compute the elastic modulus and hardness of the thin film material.

According to another aspect of the invention, there is provided a computer readable medium having computer-executable instructions for performing a method of measuring an elastic modulus and hardness of a thin film on substrate. The method includes calculating a series of experimental corrected stiffness and contact radius pairs associated with one or more presumed parameters and information obtained from a loading curve associated with the thin film and substrate. Also, the method includes calculating a series of theoretical corrected stiffness and contact radius pairs associated with the one or more presumed parameters and information obtained from the loading curve associated with the thin film and substrate. Furthermore, the method includes using results obtained from the experimental corrected stiffness and contact radius pairs and the theoretical corrected stiffness and contact radius pairs to compute the elastic modulus and hardness of the thin film material.

DETAILED DESCRIPTION OF THE INVENTION

The invention provides a technique for measuring the elastic modulus and hardness of thin film on substrate using nanoindentation technique. The contact area is estimated from the continuously measured indentation data in a single test. The analysis is based on the exact elastic solution of a layered half-space indented by a rigid punch, yet allows the overall indentation to be elasto-plastic.

Also, the invention utilizes indentation data of moderate depth relative to the film thickness, thus avoiding various measurement uncertainties (surface roughness, skin layer) associated with ultra-shallow indentation. Another feature of this invention is that it works equally well for both stiff and compliant films relative to the substrate. The effectiveness of the invention has been demonstrated in both conditions with good accuracy.

The elastic indentation of a layered half-space is mathematically a mixed boundary value problem that can be reduced to a Fredholm integral equation of the second kind:

$$H(\tau) - \frac{1}{\pi}\int_0^1 [K(y+\tau) + K(y-\tau)]H(y)dy = F_0(\tau). \tag{7}$$

The solution of the contact problem is given in terms of a function $H(\tau)$ that can be regarded as a normalized map of the pressure distribution within the contact region. The kernel of the integral equation, $K(u)$, is given by $$K(u) = \tag{8}$$
$$\frac{a}{t}\int_0^\infty \left(1 - \frac{A \cdot 2w + B \cdot \cosh(2w) + C \cdot \sinh(2w)}{D + C \cdot \cosh(2w) + B \cdot \sinh(2w) - A \cdot 2w^2}\right)\cos\left(uw\frac{a}{t}\right)dw$$

where $$A = \left(1 - \frac{M_f(1-v_f)}{M_s(1-v_s)}\right)\left(4\frac{M_f(1-v_f)}{M_s(1-v_s)}v_s - 3\frac{M_f(1-v_f)}{M_s(1-v_s)} - 1\right), \tag{9}$$

$$B = 8\frac{M_f(1-v_f)}{M_s(1-v_s)}(v_f-1)(v_s-1),$$

$$C = 3 - 4v_f + \frac{M_f(1-v_f)}{M_s(1-v_s)}$$
$$\left[2 + 3\frac{M_f(1-v_f)}{M_s(1-v_s)} - 4v_f - 4v_s\left(1 + \frac{M_f(1-v_f)}{M_s(1-v_s)} - 2v_f\right)\right],$$

$$D = \left[\frac{M_f(1-v_f)}{M_s(1-v_s)}\right]^2(4v_s-3) - 2\frac{M_f(1-v_f)}{M_s(1-v_s)}(2v_f-1)(2v_s-1) +$$
$$4v_f(2v_f-3) + 5.$$

In these expressions, $M_f$ and $M_s$ are the indentation moduli of the film and the substrate respectively; $v_f$ and $v_s$ are the respective Poisson's ratios. The right hand side of EQ. 7 is determined by the shape of the indenter. For a conical punch, for instance, $$F_0(\tau) = 1 - \gamma\tau, \tag{10a}$$

while for a spherical punch of radius R, $$F_0(\tau) = 1 - \gamma\tau \cdot \frac{\ln(1+\tau\rho) - \ln(1-\tau\rho)}{\ln(1+\rho/\gamma) - \ln(1-\rho/\gamma)}. \tag{10b}$$

In these equations, $\rho=\alpha/R$ and $\gamma$ is the ratio of the contact radius for an indentation in a film on a substrate to the contact radius for an indentation of the same depth in a homogenous half space with the same properties as the film, $$\gamma = \alpha/\alpha^H. \tag{11}$$

The relationship between the contact radius $\alpha^H$ and the indentation depth h for an elastic indentation in a homogenous half space depends on the indenter shape. For a conical punch with half included angle $\theta$, one finds that $$h = \frac{\pi a^H}{2\tan(\theta)}, \tag{12a}$$

while for a spherical punch of radius R $$h = \frac{a^H}{2}\left(\ln\frac{1+a^H/R}{1-a^H/R}\right). \quad (12b)$$

The integral equation in EQ. 7 can be solved numerically in the form of a Chebyshev series using El-Gendi's method. For conical and spherical indenters, the boundary condition of vanishing pressure at the contact periphery is expressed as $$H(1)=0. \quad (13)$$

The value of $\gamma$ is iterated until the solution satisfies EQ. 13. The basic solution to the contact problem includes the function $H(\tau)$ and the corresponding value of $\gamma$. The general form of the indentation load P required for an indenter to penetrate to a depth h is then $$P=2M_f\alpha h\int_0^1 H(\tau)d\tau. \quad (14)$$

By using EQs. 11, 12 and 14, P can be determined as a function of h for a given indenter shape. The contact stiffness is then the derivative of P with respect to h.

In an elastic indentation of a homogeneous half-space, the elastic deflection of the surface $h_s$ is related to the indentation load and the contact stiffness through EQ. 1. For a film on a substrate, $h_s$ also depends on the elastic mismatch between the film and the substrate, necessitating a dimensionless correction factor $\xi$ in the expression for the surface deflection $$h_s = \xi(a/t, M_f/M_s, \nu_f, \nu_s)\varepsilon\frac{P}{S}. \quad (15)$$

The elastic deflection of the surface is also related to the contact radius through the indenter geometry. For a conical punch with half included angle $\theta$, one has $$h_s=h-h_c=h-\alpha/\tan\theta. \quad (16)$$

Figure 1A:
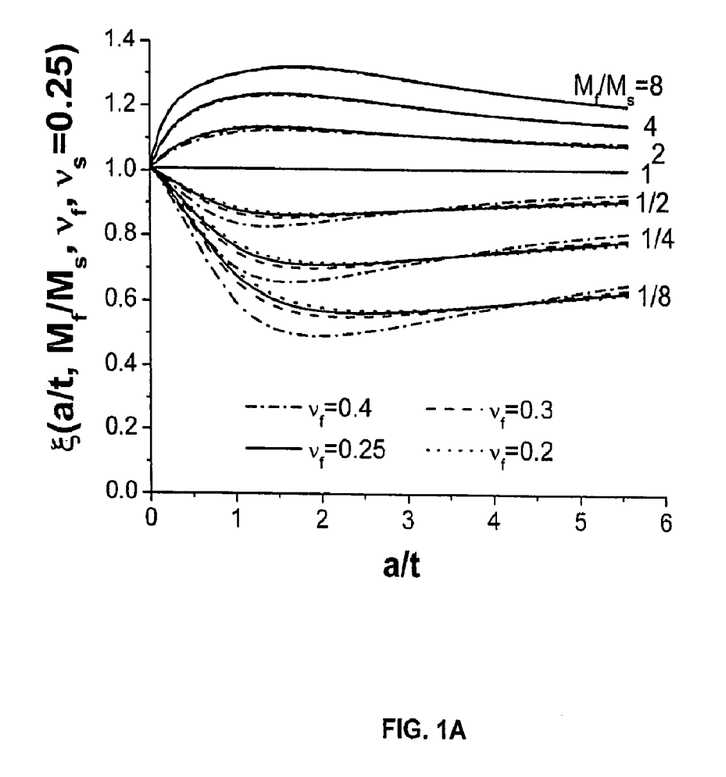
FIGS. 1A-1B are graphs illustrating the conversion function for elastic indentation as a function of contact radius normalized by film thickness for different elastic mismatches and tip geometries.

Using EQs. 11 through 16, $\xi$ can be calculated as a function of $\alpha/t$ and for different levels of elastic mismatch between film and substrate. Results for a conical indenter are shown in FIG. 1A. When the film has the same elastic properties as the substrate, $\xi$ is obviously equal to one. As $\alpha/t \to 0$, the curves also satisfy the condition $\xi \to 1$ independent of the elastic mismatch between film and substrate. This extreme case corresponds to an indentation in the homogeneous film material, for which $\xi$ should be equal to one. A similar trend is observed for very large contact areas, where the effect of the film is negligible and the indenter is effectively probing the substrate.

Figure 1B:
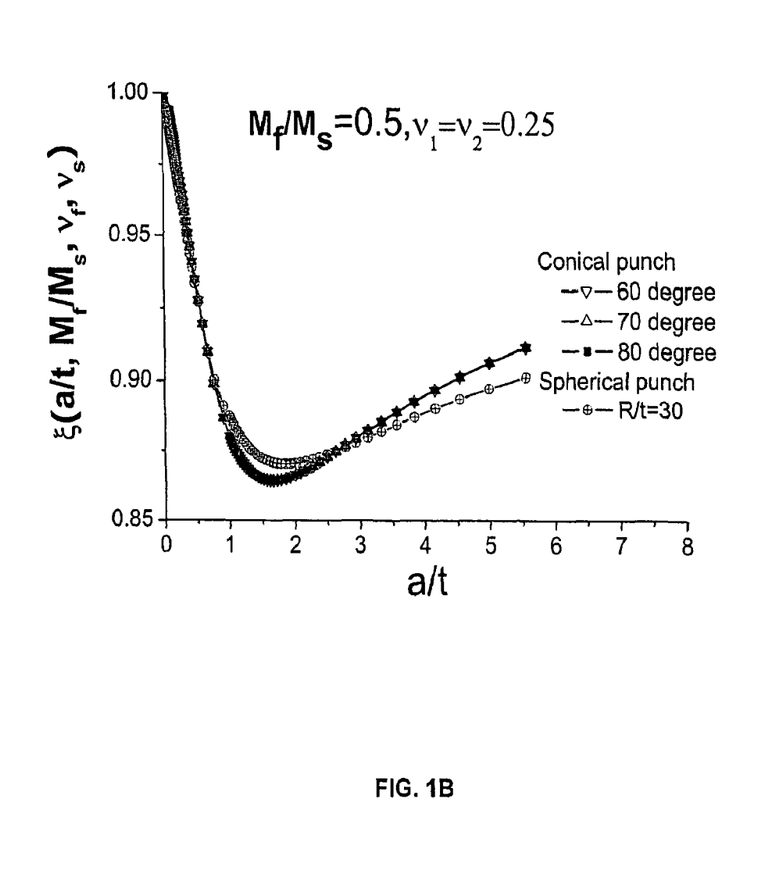

It is further evident from FIG. 1A that Poisson's ratio of the film has a relatively minor effect on the value of $\xi$, especially so if the film is stiffer than the substrate. FIG. 1B shows $\xi$ as a function of $\alpha/t$ for several conical indenters with different half included angles ($\theta=60°$, $70°$, $80°$) and for a spherical indenter (R/t=30). Evidently there is a small difference between conical and spherical indenters, but for conical indenters $\xi$ does not depend on the apex angle of the indenter.

Figure 2A:
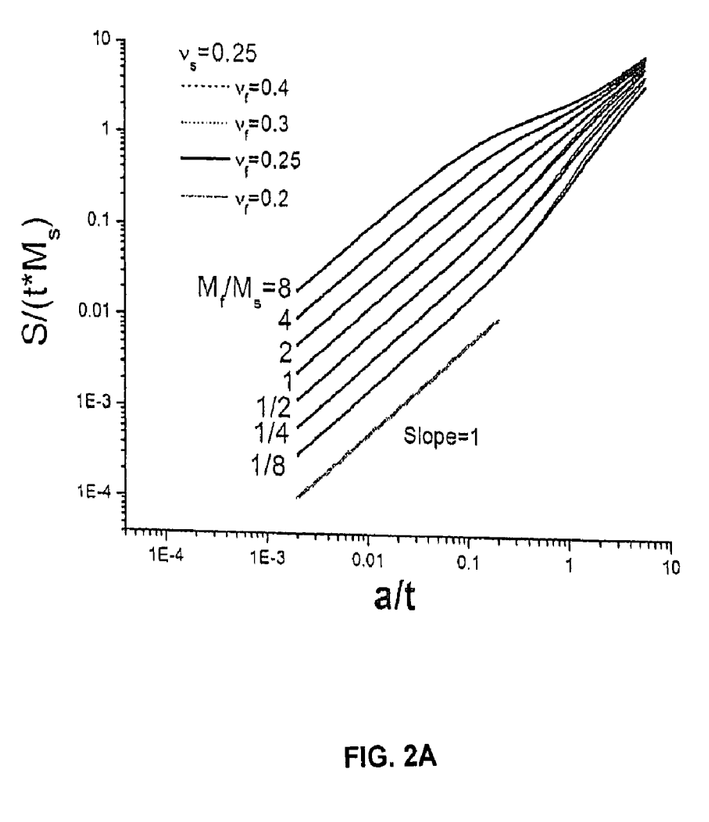
FIGS. 2A-2B are graphs illustrating normalized contact stiffness as a function of contact radius for different elastic mismatches and tip geometries.

Analysis of nanoindentation data requires the relationship between the contact stiffness and the contact radius. The calculated the contact stiffness S is calculated as a function of the contact radius for a series of film/substrate combinations for a conical indenter with a half apex angle of 70°. The results are shown on a logarithmic scale in FIG. 2A. It is clear that for small contact radii, the contact stiffness changes linearly with contact radius conform to Sneddon's equation for homogeneous materials. As the contact radius grows, the effect of the substrate becomes evident and the slopes of the curves gradually deviate from unity: the slopes increase for stiff films on compliant substrates and decrease for compliant films on stiff substrates. At very large contact radii, all curves again approach Sneddon's equation as the effect of the film fades.

Figure 2B:
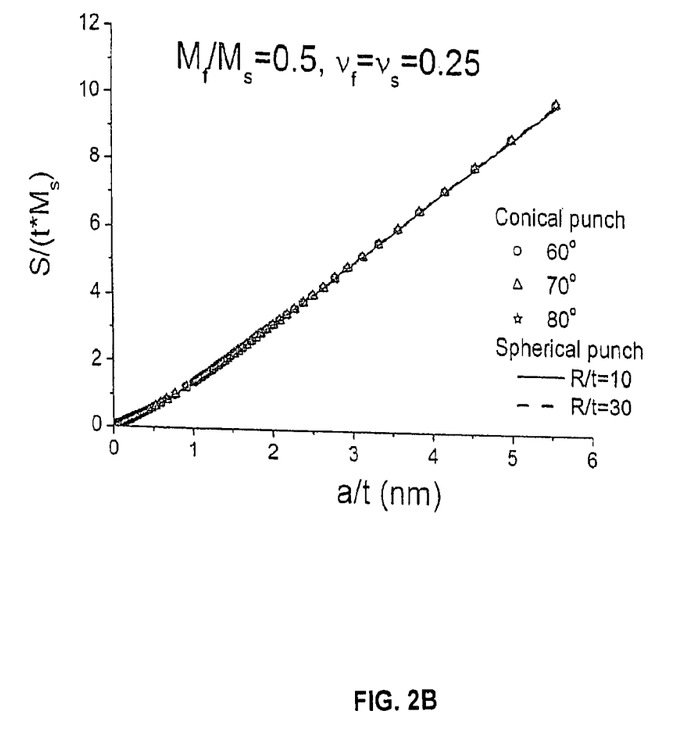

For a given contact area, the contact stiffness of an indenter on a homogeneous and isotropic half space is independent of the precise indenter shape as long as the indenter is axisymmetric and the profile of the punch can be approximated by a half-space—i.e., the apex angle $2\theta$ should be close to $180°$ for a conical punch, or $\alpha/R \Box 1$ for a spherical punch. Consequently, the contact stiffness of an arbitrary axisymmetric indenter on an elastic half space is equal to that for a flat-ended indenter with radius equal to the contact radius. The same conclusion holds true for the indentation of a film on a substrate:

In FIG. 2B, it is shown that show the S~$\alpha$ relationship calculated from Yu's solution for a given film-on-substrate assembly ($M_f/M_s=0.5$, $\nu_f=\nu_s=0.25$) indented by several conical ($\theta=60°$, $70°$, $80°$) and spherical indenters (R/t=10, 30). All curves overlap perfectly confirming that for films on substrates the contact stiffness is also independent of the indenter shape, at least within the context of linear elastic contact mechanics. When analyzing the elastic unloading process after an elasto-plastic indentation in a thin film, the relationship between contact stiffness and contact radius can be calculated without knowledge of the precise shape of the indentation, for example, without knowledge of the plastic properties of the film.

The idea of using an elastic solution in the interpretation of elasto-plastic indentation data is based on the fact that the displacement during the unloading segment of an indentation is elastic even if the material has undergone significant plastic deformation on loading—at least in the absence of time-dependent deformation or a strong Bauschinger effect. The entire unloading process can be modeled as the elastic contact between a flat surface and an effective indenter, the shape of which depends on the elastic and plastic properties of the indented material. After the discussion in the previous section, it is clear that this approach is also valid for the elasto-plastic indentation of a film on a substrate, as long as the presence of the substrate is taken into account in the elastic analysis.

There is, however, one added complication: Film thickness is well defined in an elastic indentation, but not so in an elasto-plastic indention, where the film between the indenter and the substrate has been thinned as a result of plastic flow. In order to apply Yu's solution for the indentation of a film on a substrate it is necessary to define and use an effective film thickness, $t_{eff}$, that captures this local thinning effect. Generally, $t_{eff}$ is a function of the elastic and plastic properties of both film and substrate. Dimensional analysis shows that for a given indenter shape $$\frac{t_{eff}}{t} = f\left(\frac{\sigma_y^f}{E_f}, \frac{\sigma_y^s}{E_s}, \nu_f, \nu_s, \frac{h}{t}\right), \quad (17)$$

where $\sigma_y$ refers to the flow stress of the film or the substrate depending on the superscript. One can simplify this equation as follows $$\frac{t_{eff}}{t} = 1 - \eta\left(\frac{\sigma_y^f}{E_f}, \frac{\sigma_y^s}{E_s}, v_f, v_s\right)\frac{h}{t}, \quad (18)$$

in the spirit that the effective thickness is equal to the actual film thickness for zero indentation depth and decreases monotonously with increasing depth. The dimensionless function η quantifies the local thinning of the film as a result of plastic deformation of the film. The function depends on the mechanical properties of film and substrate and on the precise indenter shape. In general, it is necessary to know η in order to use Yu's solution in the analysis of elasto-plastic indentations in thin films. One option is to calculate η numerically using a finite element model. We will demonstrate below that it is possible to experimentally determine η for a given materials system by performing a nanoindentation measurement.

Given Yu's solution, it is now possible to calculate the instantaneous contact radius during an indentation in one of two ways. First, the contact radius can be calculated directly from the instantaneous contact stiffness using the S~α relationship shown in FIG. 2A, if values for η and the indentation modulus of the film, $M_f$, are assumed. One can refer to the value of α calculated using this approach as the theoretical value of α.

Second, the contact radius can also be determined using a procedure similar to the Oliver-Pharr method. Specifically, it is assumed that the elastic deflection of the contact periphery is the same for an elasto-plastic indentation as it is for an elastic indentation. Replacing the film thickness in EQ. 16 with the effective thickness, one finds the following expression for the elastic deflection in an elasto-plastic indentation $$h_s = \xi\left(\frac{a}{(t-\eta \cdot h)}, \frac{M_f}{M_s}\right)\varepsilon\frac{P}{S}, \quad (19)$$

where the dependence on the Poisson's ratios of film and substrate is not written explicitly. Consequently the instantaneous contact radius α needs to satisfy the following implicit equation with α as the only unknown, $$a = \left(h - \xi\left(\frac{a}{(t-\eta \cdot h)}, \frac{M_f}{M_s}\right)\varepsilon\frac{P}{S}\right)\tan\vartheta. \quad (20)$$

In a real experiment, the indenter is of course not a perfect cone and it may be necessary to determine the instantaneous contact radius from $$a = \sqrt{\frac{A}{\pi}} = \sqrt{\frac{f(h - h_s)}{\pi}}, \quad (21)$$

where $f$ is the known area function of the indenter. As can be seen in FIG. 1B, the error in the correction factor ξ as a result of the imperfect tip shape is expected to be quite small. EQs. 20 or 21 can be solved numerically if η and the indentation modulus of the film are known (or assumed), and it provides another measure for the instantaneous contact radius. One can refer to this value of the contact radius as the experimental value of α.

If the contact stiffness is known at each point of the indentation loading curve—e.g., from a continuous stiffness measurement—then the two measures of the α can be calculated at every point of the indentation loading curve resulting in two continuous S~α curves. If the assumed values of η and the indentation modulus $M_f$ are correct, both curves overlap. In actual practice, $M_f$ and η can be treated as free parameters that need to be varied to achieve the best possible overlap between the two S~α curves, for example, to minimize the mean square error between the two curves.

Figure 3:
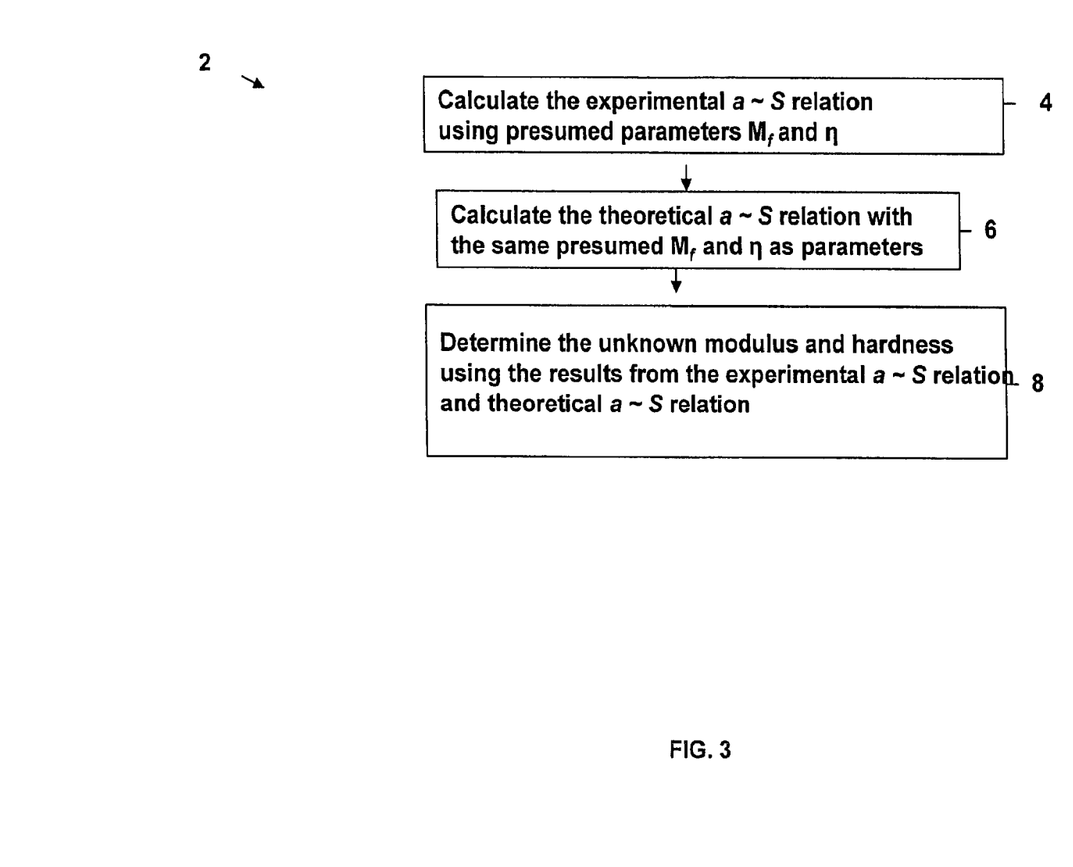
FIG. 3 is a flowchart illustrating the general steps needed to perform the invention.

FIG. 3 shows a general flowchart 2 illustrating the steps needed to perform the invention. First, one must calculate the experimental α~S relation using presumed parameters $M_f$ and η, as shown in step 4. In addition, one must calculate the theoretical α~S relation with the same presumed $M_f$ and η as parameters, as shown in step 6. The theoretical a~S relation utilizes Yu's elastic solution shown in EQ. 9-10. Using both the results from the experimental α~S relation and the theoretical α~S relation, the unknown film modulus can be determined, as shown in step 8. Once $M_f$ and η have been determined, the contact radius α can be calculated and the hardness is found as H=P/πα². This approach allows for measuring the elastic modulus and hardness of the thin film in a film-on-substrate system using nanoindentation techniques.

Figure 4:
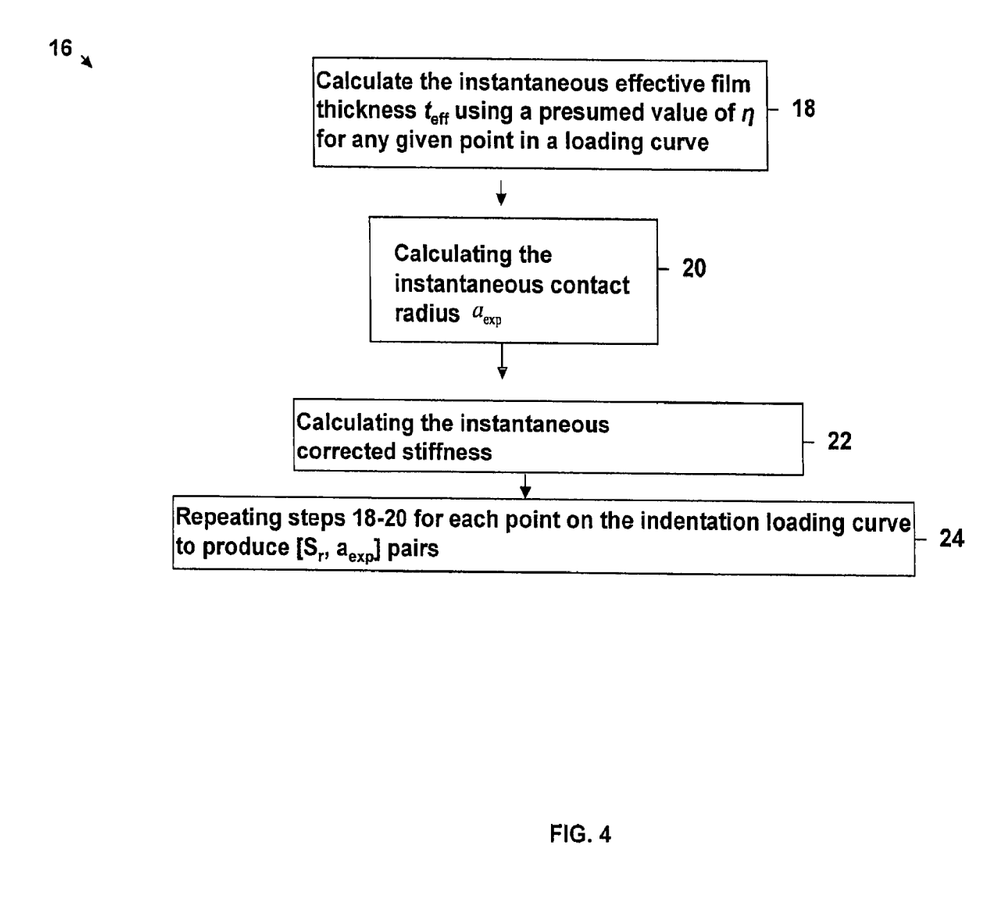
FIG. 4 is a flowchart illustrating the steps needed to calculate the experimental $\alpha$~S relation.

FIG. 4 shows a flowchart 16 illustrating the steps needed to calculate the experimental α~S relation with presumed $M_f$ and η as parameters, as shown in step 4. First, calculate the instantaneous effective film thickness $t_{eff}$ using EQ. 18 and a presumed value of η for any given point in a loading curve, as shown in step 18. The instantaneous contact radius $\alpha_{exp}$ is calculated using the following relation:

$$a_{exp} = \sqrt{\frac{1}{\pi}f\left[h - \xi\left(\frac{a_{exp}}{t_{eff}}, \frac{M_f}{M_s}\right)\varepsilon\frac{P}{S}\right]}. \quad (22)$$

where $f$ is the area function of an indenter tip, $M_f$ the presumed value of film modulus, and ξ the correction factor obtained from Yu's solution, as shown in step 20. The instantaneous corrected stiffness is calculated using the following relation:

$$S_r = \left(\frac{1}{S} - \frac{1}{S_{tip}}\right)^{-1} \quad (23)$$

to account for the compliance of the indenter tip, where $S_{tip}=2\alpha_{exp}M_{tip}$ and $M_{tip}$=1146.6 GPa for a diamond indenter, as shown in step 22. Steps 18-20 are repeated for each point on the indentation loading curve, as shown in step 24. One ends up with the continuous experimental [$S_r$, $\alpha_{exp}$] pairs that correspond to the presumed parameters $M_f$ and η in steps 18 and 20.

Figure 5:
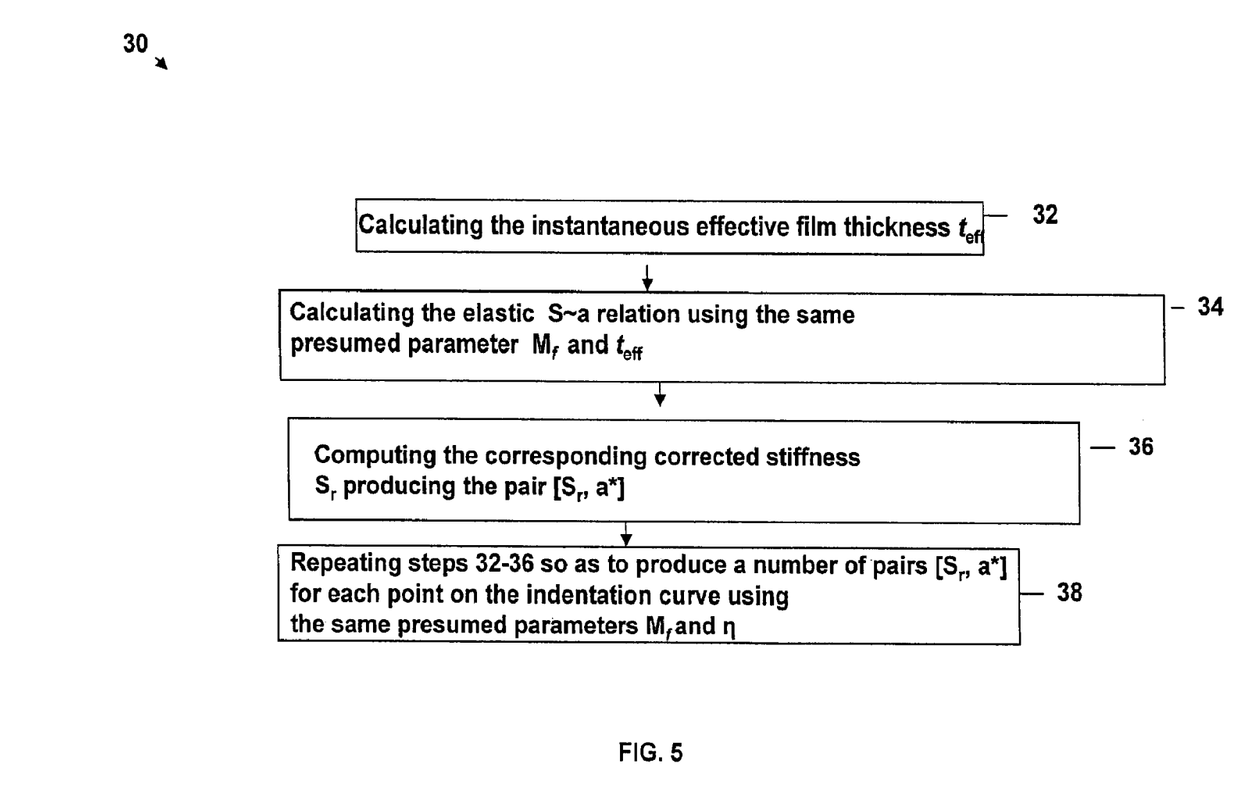
FIG. 5 is a flowchart illustrating the steps needed to calculate the theoretical $\alpha$~S relation.

FIG. 5 shows a flowchart 30 illustrating the steps needed to calculate the theoretical α~S relation with presumed parameter η. Using the same given point as in step 20, the instantaneous effective film thickness $t_{eff}$ is calculated using EQ. 19 and the presumed parameters $M_f$ and η, as shown in step 32. The elastic S~α* relation is calculated using the presumed parameter $M_f$ and $t_{eff}$ using Yu's solution associated with EQs. 12-17, as shown in step 34. Using the elastic S~α relation from step 34, the corresponding stiffness $S_r$ can be computed using EQ. 23, thus producing the pair [$S_r$, α*], as shown in step 36. Steps 32-36 are repeated so as to produce a number of pairs [$S_r$, $\alpha^*$] for each point on the indentation curve using the same presumed parameters $M_f$ and $\eta$, as shown in step 38.

Figure 6:
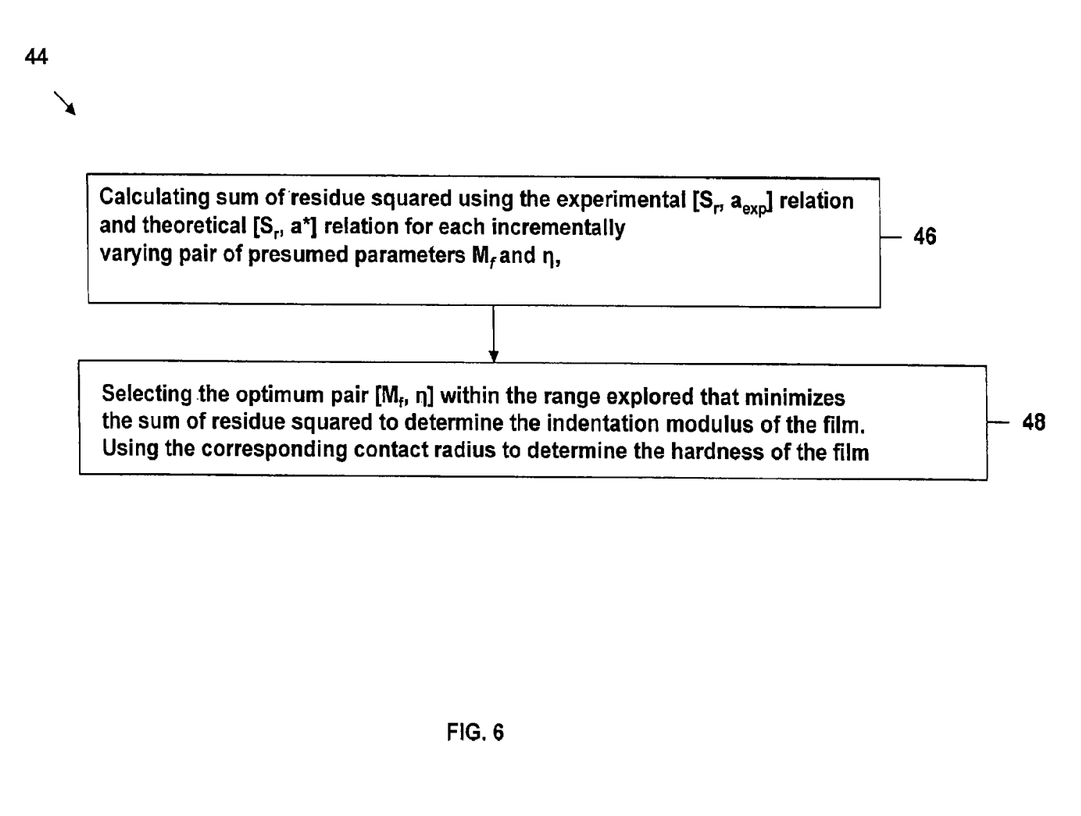
FIG. 6 is a flowchart illustrating the steps needed to extract the unknown film modulus and hardness.

FIG. 6 is a flowchart 44 illustrating the steps needed to extract unknown film modulus. The sum of residue squared $\chi^2$ is calculated using the experimental [$S_r$, $\alpha_{exp}$] relation of FIG. 4 and the theoretical [$S_r$, $\alpha^*$] relation from FIG. 6 using the following relation:

$$\chi^2 = \Sigma(\alpha_{exp} - \alpha^*)) \tag{24}$$

By incrementally varying the presumed parameters $M_f$ and $\eta$, various $\chi^2$ values are obtained using the experimental [$S_r$, $\alpha_{exp}$] relation and the theoretical [$S_r$, $\alpha^*$] relation for each varying pairs of presumed parameters $M_f$ and $\eta$, as shown in step 46. Selecting the optimum pair [$M_f$, $\eta$] within the range explored that minimizes $\chi^2$ using a standard optimization algorithm, as shown in step 48. The modulus value in the optimum pair is taken as the true indentation modulus and hardness of the film. Once $M_f$ and $\eta$ have been determined, the contact radius $\alpha$ can be calculated and the hardness is found as $H = P/\pi\alpha^2$.

The invention can also performed by a computer program that is executed in a processor associated with a computer platform in an automated fashion. The computer platform can be a network, personal computer, or embedded processing unit using various commonly know operating systems such XP, VISTA, Solaris, or the like.

Figure 7:
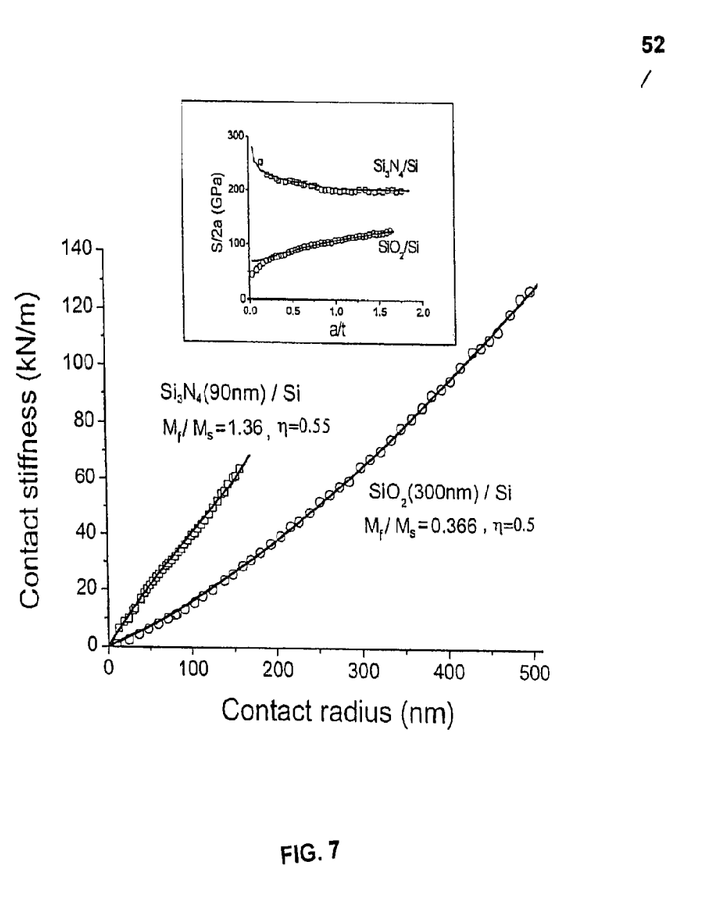
FIG. 7 is a graph illustrating experimental and theoretical contact radius as a function of contact stiffness for $SiN_x$ and $SiO_2$ samples.

FIG. 7 shows the best fit of the theoretical S~$\alpha$ relationship to the experimental S~$\alpha$ curve (markers) for both the $SiO_2$ film and the $SiN_x$ film. The inset shows the same data plotted as $S/2\alpha$ as a function of $\alpha/t$ to further highlight the goodness of fit. It is evident from both graphs that agreement between the experimental and theoretical curves is very good except for very small depths. The small discrepancy between both curves arises mainly because the initial contact between indenter and film is purely elastic. In this case, use of the total indentation depth h in the expression for the effective film thickness is inappropriate.

If the plastic depth is used in EQ. 18 instead of the total indentation depth, much better agreement is obtained. Using the plastic indentation depth indeed ensures that the method converges to the exact result for elastic indentations. Estimating the plastic indentation depth for each point on the loading curve is nontrivial, however, and involves further assumptions on the shape of the unloading curve. Furthermore, if the initial elastic contact is not included in the data analysis, virtually identical values for stiffness and hardness are obtained. Given the additional assumptions, the computational effort, and the very small benefit, it is not worthwhile to account for elastic contact in the definition of the effective depth.

The ratio of the indentation moduli for the $SiN_x$ film obtained from the fit in FIG. 7 is 1.36±0.01, yielding an indentation modulus of 242.5±0.9 GPa for the $SiN_x$ film. The corresponding value of $\eta$ is 0.55.

The fit of the experimental S–$\alpha$ data yields an indentation modulus of 65.4±0.7 GPa for the $SiO_2$ film. The corresponding value of Young's modulus is 63.1±0.7 GPa, assuming a Poisson's ratio of 0.19 for the $SiO_2$ film. Most results are in the range of 63~72 GPa, in reasonable agreement with the nanoindentation results. The value of $\eta$ obtained in the analysis is 0.5, close to the value for the $SiN_x$ film. The parameter $\eta$ was introduced to quantify the local thinning of the film caused by plastic deformation. A value of approximately 0.5 suggests that in this case the effective film thickness is best approximated by the simple average of t and t–h.

Figure 8:
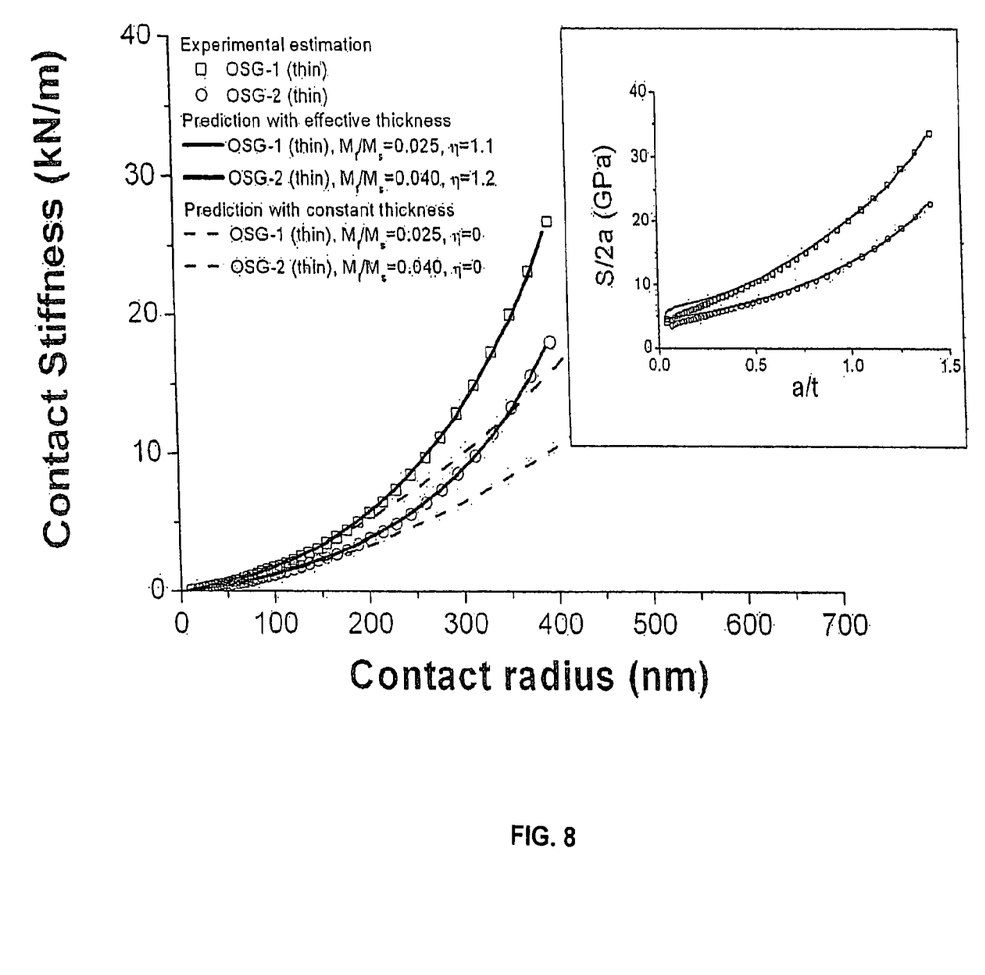
FIG. 8 is a graph illustrating experimental and theoretical contact radius as a function of contact stiffness for the various OSG films.

FIG. 8 shows the best fit of the experimental S~$\alpha$ data (hollow symbols) with the theoretical relation based on Yu's solution (solid curves) for the 280 nm OSG films. The corresponding indentation moduli are 4.45±0.19 GPa ($\eta$=1.1) and 7.07±0.46 GPa ($\eta$=1.2) for the OSG-1 and OSG-2 films, respectively. The results are in good agreement with similar films that are much thicker and readily analyzed with Oliver-Pharr method. FIG. 8 also demonstrates the importance of using the effective film thickness in the analysis. The dashed curves are theoretical predictions based on Yu's solution using the same indentation moduli as for the solid curves, but assuming a constant thickness that is equal to the total film thickness (i.e., $\eta$=0). The inset presents the same data in the form of S/2$\alpha$ versus $\alpha$/t. It is evident that the results are nearly independent of $\eta$ for shallow indentations—the plastic displacements are very small and the effect of the substrate is insignificant. This is no longer the case for larger indentations, however, and local plastic deformation has to be accounted for to obtain an accurate estimation of the contact radius. Indeed, if $\eta$ is set equal to zero and only the film modulus is allowed to vary, no good fit to the experimental data can be obtained.

The fact that $\eta$>1 for the OSG films stands in contrast with the values obtained for the $SiO_2$ and $SiN_x$ films ($\eta$~0.5). This result indicates that nanoindentation experiments on OSG films are much more sensitive to substrate effects than experiments on $SiO_2$ or $SiN_x$ films. This difference arises because of the porosity of the OSG coatings. The stress state under an indenter is highly hydrostatic and causes porous materials like OSG to densify during the indentation process. This densification leads to a local increase in the stiffness of the OSG.

Using finite element simulations, it is demonstrated that a porous material densifies in a small region below the indenter. Even though the stiffness of the material increased locally as a result of the densification, it was shown that the effect on the overall contact stiffness was not significant because the densified region was small compared to the overall volume of porous material contributing to the elastic displacement field. While this argument may be valid for porous solids in bulk form, it may be less so for the indentation of thin porous films on hard substrates. For the latter, the densified region constitutes a bigger fraction of the total film volume contributing to the elastic displacement field.

Furthermore, a hard substrate can enhance densification underneath the indenter and thus lead to a larger region of increased stiffness. Even so, it is evident from the measurements that the invention gives accurate results when the coatings are porous. The experimental values obtained for thin films using the invention are in very good agreement with the values obtained for the thick films using the Oliver-Pharr technique. This agreement also indicates that densification does not have a significant effect on the experimental indentation moduli. The values are therefore representative of the as-deposited porous OSG coatings, not the densified material.

Figure 9:
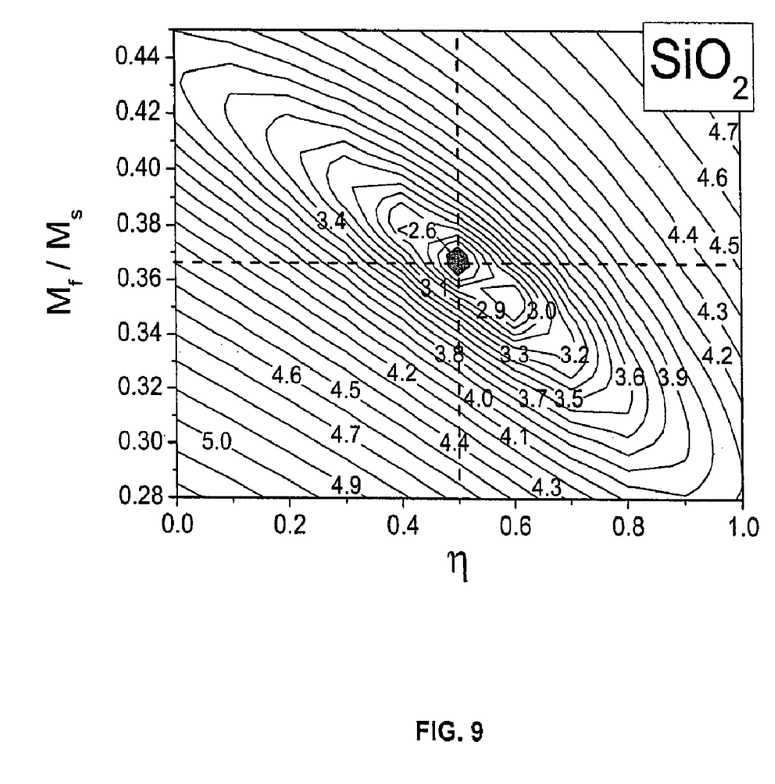
FIG. 9 is a graph illustrating a contour plot of the sum of the residues squared ($=\chi^2$) for the $SiO_2$ film.

The extraction of the indentation modulus of the film relies on a fit of the experimental S~$\alpha$ relationship with the theoretical result derived from Yu's solution using $M_f$ and $\eta$ as fitting parameters. It is possible for two or more distinct combinations of $M_f$ and $\eta$ to give a comparable quality of fit. Indeed, for the special case of a compliant film on a stiff substrate, one might expect a combination of a smaller $M_f$ and a larger $\eta$ (or vice versa) than the actual values to also give a reasonable fit to the experimental stiffness data. FIG. 9 shows a contour plot of the sum of the fit residues squared (=$\chi^2$) for the $SiO_2$ film, where the fitting parameters have been varied over a wide range. The plot shows a clear minimum corresponding to the optimum combination of $M_f$ and $\eta$, even though the contour lines are somewhat elongated as anticipated on the basis of physical arguments. Evidently, the optimum fitting parameters are well defined and unique over the range of parameters shown in FIG. 9. Similar results are also found for the $SiN_x$ and OSG coatings. One can expect the inventive technique to be robust for a wide range of coating and/or substrate properties.

The invention provides a novel technique for the analysis of nanoindentation of thin films on substrates. The technique is similar to the Oliver-Pharr method, but makes use of Yu's solution for the elastic contact of an indenter on a coated half space instead of Sneddon's solution for a homogeneous half space. This modification of the analysis procedure makes the invention applicable to thin films on substrates over a much larger range of indentation depths: Where the Oliver-Pharr analysis is applicable only in the limit of vanishing indentation depths, the invention is valid for indentation depths that are a significant fraction of the total film thickness. As such, the invention is ideal for the analysis of indentation experiments in thin films where the minimum indentation depth is set by equipment limitations. The invention is demonstrated experimentally for both compliant films on stiff substrates and the reverse combination, yielding indentation moduli in good agreement with independent measurements and literature values.

Although the present invention has been shown and described with respect to several preferred embodiments thereof, various changes, omissions and additions to the form and detail thereof, may be made therein, without departing from the spirit and scope of the invention.

What is claimed is:

1. A method, implemented using a processor, of measuring the elastic modulus and hardness of a thin film on substrate using nanoindentation technique comprising:
   calculating a series of experimental corrected stiffness and contact radius pairs associated with one or more presumed parameters and information obtained from a loading curve associated with the thin film and substrate;
   calculating a series of theoretical corrected stiffness and contact radius pairs associated with the one or more presumed parameters and information obtained from the loading curve associated with the thin film and substrate; and
   using results obtained from the experimental corrected stiffness and contact radius pairs and the theoretical corrected stiffness and contact radius pairs to compute the elastic modulus and hardness of the thin film material.

2. The method of claim 1, wherein calculating said experimental corrected stiffness and contact radius pairs comprising:
   (i) calculating the instantaneous effective film thickness using said one or more presumed parameters for a given point in said loading curve;
   (ii) calculating the experimental contact radius using said one or more presumed parameters and predefined sink-in relation from Yu's elastic solution;
   (iii) calculating the corrected stiffness using said experimental contact radius and the contact stiffness directly measured at this position; and
   (iv) repeating steps (i)-(iii) for each point on said loading curve to produce said experimental corrected stiffness and contact radius pairs.

3. The method of claim 1, wherein calculating said theoretical stiffness and contact radius pairs comprising:
   (i) calculating the instantaneous effective film thickness using said the same one or more presumed parameters for a given point in said loading curve;
   (ii) calculating a theoretical S~α relation using said one or more presumed parameters and Yu's elastic solution;
   (iii) calculating the theoretical contact radius using said corrected stiffness and said theoretical S~α relation; and
   (iv) repeating steps (i)-(iii) for each point on said loading curve to produce said theoretical corrected stiffness and contact radius pairs.

4. The method of claim 1, wherein using results obtained from said experimental corrected stiffness and contact radius pairs and said theoretical corrected stiffness and contact radius pairs to compute the elastic modulus and hardness comprising:
   calculating sum of residues squared using the experimental corrected stiffness and contact radius pairs and theoretical corrected stiffness and contact radius pairs for each incrementally varying pair of presumed parameters $M_f$ and $\eta$; and
   selecting the optimum pair of $M_f$ and $\eta$ within a sufficiently wide range explored that minimizes the sum of residues squared to determine the elastic modulus of the thin film, wherein once the optimum pair of $M_f$ and $\eta$ is determined, the corresponding contact radius is used to calculate the hardness of the film.

5. The method of claim 1, wherein a substrate comprising silicon is used as the substrate on which the elastic modulus and hardness of the thin film is measured.

6. The method of claim 1, wherein a thin film comprising $SiO_2$ and $SiN_x$ is used as the thin film for which the elastic modulus and hardness is being measured.

7. The method of claim 1, wherein a thin film comprising OSG porous films is used as the thin film for which the elastic modulus and hardness is being measured.

* * * * *